United States Patent [19]

Hill et al.

[11] 4,124,759

[45] Nov. 7, 1978

[54] PREPARATION OF AURANOFIN BY O-ACETYLATION

[75] Inventors: David T. Hill, North Wales, Pa.; Ivan Lantos, Blackwood, N.J.; Blaine M. Sutton, Hatboro, Pa.

[73] Assignee: SmithKline Corporation, Philadelphia, Pa.

[21] Appl. No.: 812,016

[22] Filed: Jun. 30, 1977

[51] Int. Cl.$^2$ ............................................ C07H 23/00
[52] U.S. Cl. ................................... 536/121; 424/180; 536/4; 536/122
[58] Field of Search ...................................... 536/4, 121

[56] References Cited

U.S. PATENT DOCUMENTS

| 3,635,945 | 1/1972 | Nemeth et al. | 536/4 |
| 3,843,626 | 10/1974 | Sutton | 536/4 |
| 3,985,727 | 10/1976 | Daniels | 536/4 |

OTHER PUBLICATIONS

Sutton et al., J. Med. Chem. 15, 1095 (1972).

*Primary Examiner*—Johnnie R. Brown
*Assistant Examiner*—Blondel Hazel
*Attorney, Agent, or Firm*—William H. Edgerton

[57] ABSTRACT

Auranofin is prepared by direct O-acetylation of S-triethylphosphinegold 1-thio-$\beta$-D-glucopyranoside.

4 Claims, No Drawings

PREPARATION OF AURANOFIN BY O-ACETYLATION

This invention comprises a method for preparing auranofin, S-triethylphosphinegold 2,3,4,6-tetra-O-acetyl-1-thio-β-D-glucopyranoside, which involves direct O-acetylation of S-triethylphosphinegold 1-thio-β-D-glucopyranoside.

PRIOR ART STATEMENT

Auranofin has been described as prepared by a number of synthetic procedures usually by the reaction of the alkali metal salt of 2,3,4,6-tetra-O-acetyl-1-thio-β-D-glucopyranose with triethylphosphinegold chloride. See U.S. Pat. No. 3,635,945 and J. Med. Chem. 15: 1095 (1972). There is no suggestion in the art of the process here claimed.

This process is based on direct O-acetylation of S-triethylphosphinegold 1-thio-β-D-glucopyranoside using a tertiary organic base and acetic anhydride under moderate conditions. The use of certain traditional O-acylation methods on desacetyl auranofin such as acetyl chloride plus alkali in aqueous miscible solvents causes extensive decomposition of the sugar gold complex which serves as starting material.

The process here described comprises reacting S-triethylphosphinegold 1-thio-β-D-glucopyranoside with an excess of a tertiary organic amine base such as a tertiary heterocyclic amine which has basic characteristics for example pyridine, picoline, lutidine, N-methyl-tetramethylpiperidine, 1,8-bis(dimethylamino)naphthalene or N-methylpiperidine or a triloweralkylamine with similar basic properties such as tributylamine, triamylamine or triethylamine. If the tertiary amine has suitable solvent properties at the temperature of the reaction, such as the preferred pyridine, it may be used in excess as the solvent. Otherwise, a slight to moderate excess of the tertiary amine may be present with an organic solvent in which the starting materials are soluble and to which it is chemically inert. Such solvents are ethyl ether, dioxane, dimethylacetamide, dimethyl sulfoxide, dimethylformamide, benzene, methylene chloride, carbon tetrachloride and chloroform. The solvent or tertiary amine should be as water free as possible for commercial conditions.

The phosphinegold complex together with the tertiary organic amine and acetic anhydride in excess, optionally with an inert organic solvent present, are reacted at temperatures ranging from about −25° to the reflux temperature of the reaction mixture. Best results are from 0° to room temperature. The reaction mixture is allowed to stand until the reaction is complete such as overnight for low temperatures to up to 1-2 hours on the steam bath. The time and temperature of the reaction are not particularly crucial to the reaction but low temperatures for longer periods of time such as −25° to 0° for from 6-24 hours give good yields of auranofin.

The reaction is worked up by methods commonly used such as removing the volatile materials, excess amine and solvent usually at reduced pressure. The residue is then extracted with an organic solvent in which auranofin is soluble such as methylene chloride or chloroform. The washed and dried extracts are again evaporated and the residue purified by chromatography. As a less desirable alternative, the reaction of this invention can be run using acetyl chloride in tertiary base as described above. Usually when acetyl chloride is used a smaller excess of acylating agent is used along with correspondingly lower reaction temperatures.

The following example is illustrative of this invention. Temperatures are on the Centigrade scale.

EXAMPLE 1

A pyridine solution (30 ml) of acetic anhydride (7.5 ml) and the 3.0 g (5.9 mmoles) of S-triethylphosphinegold 1-thio-β-D-glucopyranoside was stirred overnight at 0° and then at room temperature for 3 hours. After heating on a steam bath (10 minutes) the volatile materials were removed at reduced pressure and the resultant brown oil poured into ice water (250 ml). In running this reaction, one will recognize with experience whether the starting material is being decomposed at a chosen temperature range. The mixture was extracted with chloroform (3 × 20 ml) and the combined chloroform extracts washed with water (2 × 20 ml), dried over magnesium sulfate, filtered and the solvent removed at reduced pressure. Column chromatography gave two fractions (silica gel/chloroform). The first fraction, after crystallization from methanol-water, gave auranofin, m.p. 99°–101°; $[\alpha]_D^{25}$ (1% $CH_3OH$) = −54.2.

Substituting slightly in excess of 4 molar equivalent quantities of acetyl chloride in the above procedure gives auranofin.

What is claimed is:

1. The method of preparing S-triethylphosphinegold 2,3,4,6-tetra-O-acetyl-1-thio-β-D-glucopyranoside comprising reacting S-triethylphosphinegold 1-thio-β-D-glucopyranoside with an excess of acetic anhydride or about 4 mole equivalents of acetyl chloride in the presence of an excess of a tertiary organic amine base.

2. The method of claim 1 in which the tertiary organic amine base is pyridine and acetic anhydride is used.

3. The method of claim 1 in which the tertiary organic amine base is triethylamine and acetic anhydride is used.

4. The method of claim 2 in which the base serves as solvent and the reaction is run at a temperature of from about 0° to the temperature of the steam bath.

* * * * *